United States Patent
Omori

(10) Patent No.: US 8,814,541 B2
(45) Date of Patent: Aug. 26, 2014

(54) TURBO BLOOD PUMP

(75) Inventor: Masayoshi Omori, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 131 days.

(21) Appl. No.: 13/255,661

(22) PCT Filed: Mar. 8, 2010

(86) PCT No.: PCT/JP2010/053774
§ 371 (c)(1),
(2), (4) Date: Sep. 9, 2011

(87) PCT Pub. No.: WO2010/104031
PCT Pub. Date: Sep. 16, 2010

(65) Prior Publication Data
US 2011/0318204 A1     Dec. 29, 2011

(30) Foreign Application Priority Data

Mar. 9, 2009  (JP) ................. 2009-055346

(51) Int. Cl.
| | |
|---|---|
| *F04B 17/00* | (2006.01) |
| *A61M 1/10* | (2006.01) |
| *F04D 29/24* | (2006.01) |
| *F04D 13/02* | (2006.01) |
| *F04D 29/048* | (2006.01) |
| *F04D 29/046* | (2006.01) |

(52) U.S. Cl.
CPC ............... *A61M 1/101* (2013.01); *F04D 29/24* (2013.01); *F04D 13/027* (2013.01); *F04D 29/048* (2013.01); *F04D 29/0467* (2013.01); *A61M 1/1015* (2013.01); *A61M 1/1031* (2013.01)
USPC .......................... 417/420; 417/423.1; 416/183

(58) Field of Classification Search
CPC ....... F04D 7/02; F04D 29/22; F04D 29/2216; F04D 29/24
USPC .................. 417/420, 423.1, 423.15; 416/183
See application file for complete search history.

(56) References Cited

U.S. PATENT DOCUMENTS 5,322,413 A * 6/1994 Vescovini et al. ............. 415/102
6,135,710 A * 10/2000 Araki et al. ................... 415/206

(Continued)

FOREIGN PATENT DOCUMENTS

| EP | 0834326 | 4/1998 |
|---|---|---|
| JP | 4-241872 | 8/1992 |

(Continued)

*Primary Examiner* — Peter J Bertheaud
*Assistant Examiner* — Dominick L Plakkoottam
(74) *Attorney, Agent, or Firm* — Hamre, Schumann, Mueller & Larson, P.C.

(57) ABSTRACT

An impeller is provided with a rotating shaft rotatably supported at the upper and lower ends thereof by an upper bearing and a lower bearing, a plurality of vanes connected to the rotating shaft on the inner circumferential edge side thereof, an annular coupling portion connecting outer circumferential edges of the vanes, and driven magnet portions provided in a lower portion of the annular coupling portion. The rotation of a rotor is transmitted to the impeller through magnetic coupling between the driven magnets and drive magnets provided to the rotor. The upper edge of each of the vanes has a bend point, and an angle α formed by a peripheral upper vane edge and an angle β formed by a central upper vane edge relative to the downward direction of the rotating shaft are both acute angles and have a relationship of α<β. An inner wall surface of a housing in a region opposed to the upper edge of the vane has a shape following the upper edge of the vane.

10 Claims, 7 Drawing Sheets

(56) References Cited

U.S. PATENT DOCUMENTS

| | | | |
|---|---|---|---|
| 6,752,602 B2* | 6/2004 | Eistrup et al. | 417/356 |
| 2002/0031436 A1* | 3/2002 | Maeda et al. | 417/420 |
| 2002/0076322 A1* | 6/2002 | Maeda et al. | 415/170.1 |
| 2003/0147754 A1 | 8/2003 | Eistrup et al. | |
| 2004/0091354 A1* | 5/2004 | Araki et al. | 415/206 |
| 2008/0240947 A1 | 10/2008 | Allaire et al. | |
| 2009/0326649 A1* | 12/2009 | Omori | 623/3.13 |

FOREIGN PATENT DOCUMENTS

| | | |
|---|---|---|
| JP | 10-99429 | 4/1998 |
| JP | 2002-85553 | 3/2002 |
| JP | 2002-85554 | 3/2002 |
| JP | 2002-512333 | 4/2002 |
| JP | 2003-525708 | 9/2003 |
| JP | 2008-183229 | 8/2008 |
| JP | 2008183229 A * | 8/2008 |
| WO | WO 95/09984 | 4/1995 |

* cited by examiner

TURBO BLOOD PUMP

TECHNICAL FIELD

The present invention relates to a blood pump for transporting blood, and in particular, to a turbo blood pump that subjects blood to a centrifugal force by the rotation of an impeller to allow the blood to flow.

BACKGROUND ART

Blood pumps are indispensable for conducting extracorporeal blood circulation in an artificial heart and lung apparatus and the like. A turbo blood pump is known as one of the blood pumps. In the turbo blood pump, an impeller is rotated in a pump chamber having inlet and outlet ports to generate a differential pressure for transporting blood with a centrifugal force.

The turbo blood pump can be miniaturized and reduced in weight and cost due to the operation principle thereof. Furthermore, the turbo blood pump is excellent in durability since it is not affected by a tube damage or the like unlike a roller-pump type blood pump; therefore, the turbo blood pump can be used preferably for continuous operation for a long period of time. Thus, the turbo blood pump is becoming mainstream as a blood pump for an extracorporeal circulation circuit in an artificial heart and lung apparatus or a cardioassist apparatus after open-heart surgery.

For example, a turbo blood pump described in Patent Document 1 has a configuration shown in FIG. 6. In this figure, reference numeral 1 denotes a housing, which forms a pump chamber 2 for allowing blood to pass and flow therethrough, and is provided with an inlet port 3 that communicates with an upper portion of the pump chamber 2 and an outlet port 4 that communicates with a side portion of the pump chamber 2. In the pump chamber 2, an impeller 5 is placed. FIG. 7A is a top view of the impeller 5. The impeller 5 has six vanes 6, a rotating shaft 7, and a ring-shaped annular coupling portion 8.

As shown in FIG. 7A, the six vanes include vanes of two kinds of shapes: long main vanes 6a and short sub vanes 6b, which are placed alternately. The main vanes 6a and the sub vanes 6b are referred to as the vanes 6 collectively. Ends of the main vanes 6a on a center side are coupled to the rotating shaft 7 via arms 18, and ends thereof on a circumferential edge side are coupled to the annular coupling portion 8. The ends of the sub vanes 6b on the center side are free ends not coupled to the rotating shaft 7, and only ends thereof on the circumferential edge side are coupled to the annular coupling portion 8. The reason why all the vanes 6 are not coupled to the rotating shaft 7 is to prevent the increasing number of the arms 18 from interfering with a flow path. A minimum number of the arms 18 sufficient for transmitting the rotation of the impeller to the rotating shaft 7 may be provided. As the cross-sectional shape of the vanes 6 in FIG. 6, only those which are taken along the main vanes 6a in FIG. 7A are illustrated, for the sake of convenience.

Although not shown precisely in FIG. 7A, the vanes 6 (both the main vanes 6a and the sub vanes 6b) have a three-dimensional curved surface shape as shown in FIG. 7B. Specifically, a line segment connecting between an upper end of the vane 6 and a lower end thereof on an inlet side (center portion of the impeller 5) on which blood flowing from the inlet port 3 comes into contact with (bumps against) the vane 6 is referred to as a vane inlet line K. Further, a line segment connecting between an upper end of the vane 6 and a lower end thereof on an outlet side (outer circumferential edge portion of the impeller 5) on which blood leaves from the vane 6 is referred to as a vane outlet line L. The vane inlet line K is twisted with respect to the rotating shaft 7, and the vane outlet line L is twisted with respect to the vane inlet line K.

For example, the vane outlet line L is parallel to the direction of the rotating shaft 7, whereas an angle γ formed by the vane inlet line K with respect to the direction of the rotating shaft 7 is set to be about 30°, for example. The vane 6 formed of planes connecting the vane inlet line K to the vane outlet line L between an inlet portion and an outlet portion has a three-dimensional curved surface of a twisted shape. Thus, a blood pump with hemolysis reduced can be realized, which has a sufficient ejection ability and suppresses cavitation (peeling, whirlpool of flow) generated on the outlet side of the vane 6.

As shown in FIG. 6, the rotating shaft 7 is supported rotatably by an upper bearing 9 and a lower bearing 10 provided at a housing 1. The annular coupling portion 8 is provided with a magnet case 11 in which driven magnets 12 are embedded. Each of the driven magnets 12 has a cylindrical shape, and six driven magnets 12 are placed at a predetermined interval in a circumferential direction of the annular coupling portion 8. The annular coupling portion 8 and the magnet case 11 form a cylindrical inner circumferential surface.

A rotor 13 is placed below the housing 1. The rotor 13 includes a drive shaft 14 and a substantially cylindrical magnetic coupling portion 15, which are coupled to each other. Although not shown, the drive shaft 14 is supported rotatably, and is coupled to a rotation drive source such as a motor to be rotated. Furthermore, the relative positional relationship is kept constant between the rotor 13 and the housing 1 by an element (not shown). Drive magnets 16 are embedded in an upper surface portion of the magnetic coupling portion 15. The drive magnets 16 have a cylindrical shape, and the six drive magnets 16 are placed at a predetermined interval in a circumferential direction.

The drive magnets 16 are placed so as to be opposed to the driven magnets 12 with a wall of the housing 1 interposed therebetween. Thus, the rotor 13 and the impeller 5 are coupled to each other magnetically, and when the rotor 13 is rotated, the impeller 5 is rotated through magnetic coupling.

A surface of the annular coupling portion 8, on which the driven magnets 12 are set, is an inclined surface that is not orthogonal to the rotating shaft 7 and has a predetermined angle. Similarly, an upper surface of the magnetic coupling portion 15, on which the drive magnets 16 are set, is an inclined surface. Thus, the driven magnets 12 and the drive magnets 16 form magnetic coupling on a surface inclined with respect to the rotating shaft of the impeller 5, whereby the magnetic attractive force acting on an area between the impeller 5 and the rotor 13 is generated in a direction inclined with respect to the rotating shaft of the impeller 5. Consequently, the downward load on the lower bearing 10 is reduced. Thus, the friction of the lower bearing 10 is alleviated, so that the strength of magnetic coupling can be made sufficiently large.

As is understood from the figure, the impeller 5 has a space 19 in a region inside the annular coupling portion 8, allowing a flow path passing vertically through the vanes 6 to be formed. A base 20 having a cylindrical outer circumferential surface, which protrudes upward, i.e., to the inside of the pump chamber 2, is formed at the center in a bottom portion of the housing 1. The base 20 is formed so as to fill the space 19 in the region inside the driven magnets 12 and the annular coupling portion 8 in the lower portion of the impeller 5, which minimizes the volume of the space. Thus, the priming volume in the pump chamber 2 is reduced.

The upper bearing 9 is placed at a position below the inlet port 3, penetrating the pump chamber 2. Three bearing pillars 17 are provided on the inner surface in a lower end portion of the inlet port 3, and extend diagonally downward to penetrate the pump chamber 2, and the upper bearing 9 is supported by the tip end of the bearing pillars 17 in the center portion of the flow path cross-section of the inlet port 3. The lower bearing 10 is provided at the center in an upper surface portion of the base 20.

In the turbo blood pump with the above configuration, the impeller 5 is supported vertically by the upper bearing 9 and the lower bearing 10. Therefore, the supported state of the impeller 5 is stable, and hence, the rotation state is stable, whereby the stable blood supply can be realized. Further, the annular coupling portion 8 does not have a size covering the entire bottom surface of the housing 1, and the impeller 5 has a space in a region spreading between the rotating shaft 7 and the annular coupling portion 8. Thus, the impeller 5 is lightweight, and a small drive force suffices.

Further, the formation of a blood clot in a stagnant portion of blood is a problem caused by using the blood pump for a long time. For example, blood stagnates easily in a lower portion of an impeller of a conventional blood pump, and there is a possibility that a blood clot may be formed. However, the above-mentioned configuration disclosed by Patent Document 1 is also effective for eliminating the stagnant portion of blood. The reason for this is as follows. Since a flow path passing vertically through the vanes 6 is formed in a region spreading between the rotating shaft 7 and the annular coupling portion 8, blood flowing to the lower portion of the impeller 5 passes through the vicinity of the lower bearing 10 to reach the vanes 6 and flows out in an outer diameter direction of the vanes 6. Such a flow function suppresses the stagnation of blood.

However, in the case of the configuration of the blood pump disclosed by Patent Document 1, a number of blood clots are formed on the periphery of the rotating shaft 7, for example, in the vicinity of the lower bearing 10 on the upper surface of the base 20. As a result of an experiment, the following is found: although blood in a gap between the impeller 5 and the bottom surface of the housing 1 flows toward the center of the impeller 5, the flow rate of a blood stream becomes small in a gap portion 21 on the inner side of the annular coupling portion 8, and in particular, a blood stream at a sufficient flow rate is not formed in the vicinity of the lower bearing 10 on the upper surface of the base 20. Therefore, the blood stagnates, and the heat generated by the lower bearing 10 serves as a main factor for hemolysis. Further, due to the above-mentioned stagnation, a blood clot is formed easily in the vicinity of the lower bearing.

In order to solve the above-mentioned problems, Patent Document 2 discloses a turbo blood pump of a configuration as shown in the cross-sectional view of FIG. 8. The blood pump is different from the conventional example shown in FIG. 6 in the configuration of an impeller 22. FIG. 9 is a top view of the impeller 22, and FIG. 10 is a cross-sectional view thereof.

As is clearly shown in FIGS. 9 and 10, the impeller 22 has a blockade member 23 placed below the vanes 6 in a region spreading between the rotating shaft 7 and the annular coupling portion 8. The blockade member 23 blocks a flow path passing from a space in the region, which spreads between the rotating shaft 7 and the annular coupling portion 8, to the vanes 6, while leaving a part of an opening 24 around the rotating shaft 7. By providing the blockade member 23, the formation of a blood clot around the rotating shaft 7, for example, in the vicinity of the lower bearing 10 on the upper surface of the base 20 can be suppressed.

More specifically, by providing the blockade member 23, the blood in the gap between the impeller 22 and the bottom surface of the housing 1 flows toward the center of the impeller 5 along the lower surface of the blockade member 23, and thereafter, rises through the opening 24 of the blockade member 23. At this time, a blood stream with a sufficient flow rate is formed adjacent to the lower bearing 10 along the rotating shaft 7, which prevents the stagnation of blood. Thus, the region where blood stagnates, forming a blood clot according to the configuration of Patent Document 1, also is ready to be washed away at all times, so that the formation of a blood clot is suppressed.

PRIOR ART DOCUMENT

Patent Document

Patent Document 1: JP 2002-85554 A
Patent Document 2: JP 2008-183229 A

DISCLOSURE OF INVENTION

Problem to be Solved by the Invention

Although the blockade member 23 provided at the blood pump disclosed by Patent Document 2 exhibits the effect of suppressing a blood clot in the vicinity of the lower bearing 10, the effect of cleaning is not sufficiently obtained in the vicinity of the upper bearing 9.

The reason for the above is as follows: in the turbo pump, the vanes 6 do not reach the shaft center portion, where a flow is likely to stagnate. Further, the gap between the impeller 5 and the upper inner wall of the housing 1 is large, and hence, the effect of cleaning by a so-called secondary flow is weak. That is, a flow of blood (secondary flow) passing through the gap between the upper surface of the impeller 22 and the inner wall surface of the housing 1 to return to the inlet side of the vanes 6 is unlikely to reach the vicinity of the upper bearing 9. Therefore, it cannot be said that the formation of a blood clot is suppressed sufficiently in the vicinity of the upper bearing.

An object of the present invention is to provide a turbo blood pump in which a rotating shaft of an impeller is supported by upper and lower bearings, and the effect of cleaning by a blood stream in the vicinity of the upper bearing is obtained sufficiently.

Means for Solving Problem

A turbo blood pump of the present invention, includes: a housing having a pump chamber, an inlet port, and an outlet port; an impeller supported rotatably in the pump chamber; a rotatable rotor provided in an outside lower portion of the housing; and a drive force transmitting element for rotating the impeller. The impeller includes: a rotating shaft supported rotatably by an upper bearing and a lower bearing at upper and lower ends; a plurality of vanes connected to the rotating shaft on an inner circumferential edge side; an annular coupling portion coupling an outer circumferential edge side of each of the vanes; and a driven magnet portion placed in a lower portion of the annular coupling portion. The drive force transmitting element is formed of magnetic coupling between the driven magnet portion and a drive magnet portion provided at the rotor.

In order to solve the above-mentioned problems, the turbo blood pump of the present invention is characterized in that an upper edge of each of the vanes is bent, and a peripheral upper vane edge on an outer circumferential edge side with respect to a bend point and a central upper vane edge on a center side with respect to the bend point are formed on the vane, when an angle formed by the peripheral upper vane edge relative to a downward direction of the rotating shaft direction is defined as a peripheral upper vane edge angle α, and an angle formed by the central upper vane edge relative to the downward direction of the rotating shaft direction is a central upper vane edge angle β, the peripheral upper vane edge angle α and the central upper vane edge angle β are both acute angles and have a relationship of α<β, and an inner wall surface of the pump chamber of the housing in a region opposed to an upper edge of the vane has a shape along the upper edge of the vane.

Effects of the Invention

According to the above-mentioned configuration, the central upper vane edge angle β is set to be smaller than the peripheral upper vane edge angle α, and the inner wall surface of the housing has a shape following the central upper vane edge. Thus, the gap between an upper portion of the impeller and an upper inner wall surface of the housing becomes small. This improves the flow state in the vicinity of the upper bearing and enhances the effect of cleaning by a blood stream. This is because a state is obtained easily where a flow of blood, which comes out of the outlet side of the vanes and passes through the gap between the upper surface of the impeller and the inner wall surface of the housing to return to the inlet side of the vanes, reaches the vicinity of the upper bearing.

DESCRIPTION OF THE INVENTION

Figure 1:
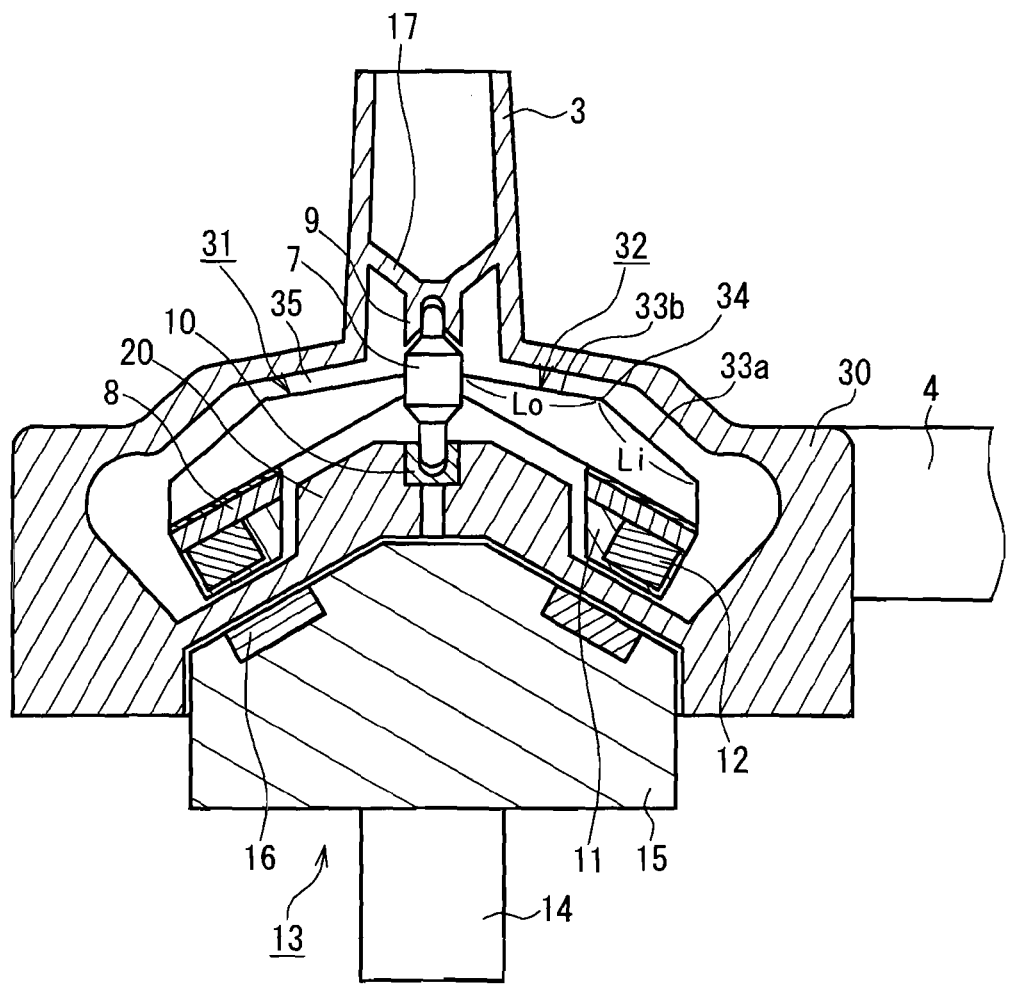
FIG. 1 is a cross-sectional view of a turbo blood pump in Embodiment 1 of the present invention.

The turbo blood pump of the present invention can assume the following embodiments based on the above-mentioned configuration.

Specifically, it is preferred that at least a part of the upper bearing is placed in the inlet port.

Further, it is preferred that an inner circumferential edge side of the vane extends to a position of the rotating shaft in such a manner that the vane is coupled to the rotating shaft directly. According to this configuration, the flow state in the center portion of the impeller becomes satisfactory, and the effect of cleaning in the vicinity of the upper bearing is enhanced further.

Further, it is preferred that when a line segment connecting an upper end of each of the vanes to a lower end thereof on an inlet side on which blood flowing from the inlet port comes into contact with the vane is defined as a vane inlet line K, and a line segment connecting an upper end of each of the vanes to a lower end thereof on an outlet side on which blood leaves from the vane is defined as a vane outlet line L, each of the vanes has a three-dimensional curved surface shape in which the vane inlet line K is twisted with respect to the rotating shaft, and the vane outlet line L is twisted with respect to the vane inlet line K, and the vane has a predetermined twisted shape in a predetermined range of a region on the outer circumferential edge side and forms a linear shape in a region on an inner circumferential edge side.

If the leading end and the trailing end of the vane have a twisted relationship as in the above-mentioned configuration, even when an end of an inner circumferential edge side is allowed to extend as it is, the end does not pass through the rotating shaft, and the impeller is bent extremely. Then, only in a portion influencing the ejection ability of the pump and hemolysis, a vane is provided with a twist in the same way as in a conventional example, and a portion extending to the rotating shaft is allowed to extend linearly with a twist eliminated, whereby a reasonable shape can be formed.

Further, it is preferred that when a length of the region having the predetermined twisted shape on the outer circumferential edge side of the vane is defined as Ptw and a length of the region having the linear shape of the vane is defined as Pst, the length Ptw and the length Pst are adjusted so as to satisfy a relationship: $0.58 < Ptw/(Ptw+Pst) < 0.80$.

Further, it is preferred that the vane upper edge angle α is set in a range of 30° to 60°, and the vane upper edge angle β is set in a range of 70° to 90°.

Further, it is preferred that a ratio Lo/Li of a length Lo of a region of the central upper vane edge with respect to a length Li of a region of the peripheral upper vane edge in a radial direction of the impeller is set in a range of 0.75 to 3.20

Further, it is preferred that the impeller includes a blockade member placed below the vanes in a region spreading between the rotating shaft and the annular coupling portion, and the blockade member blocks a space in the region spreading between the rotating shaft and the annular coupling portion while leaving an opening at least around the rotating shaft.

In this case, it is preferred that a base having a cylindrical outer circumferential surface which protrudes upward is formed at the center in a bottom portion of the housing so as to fill a space in a region of a lower portion of the impeller surrounded by a cylindrical inner circumferential surface formed by the annular coupling portion and the driven magnet portion. The base is provided with the lower bearing, the opening of the blockade member has a circular shape concentric to the rotating shaft, and when a diameter of the opening of the blockade member is d, and a diameter of the cylindrical outer circumferential surface of the base is D, the diameter d of the opening is set in a range of $0.12D \leq d \leq 0.3D$.

Further, sub vanes are placed between the vanes, an outer circumferential edge side of each of the sub vanes being connected to the annular coupling portion and an inner circumferential edge side of each of the sub vanes being a free end.

Hereinafter, a turbo blood pump in an embodiment of the present invention will be described with reference to the drawings.

Embodiment 1

FIG. 1 is a cross-sectional view showing a turbo blood pump in Embodiment 1 of the present invention. The basic configuration of the turbo blood pump is similar to that of the conventional example shown in FIGS. 6, 7A, and 7B. Therefore, elements similar to those shown in FIGS. 6 and 7 are denoted with the same reference numerals as those therein, and repeated descriptions thereof are omitted.

Figure 2:
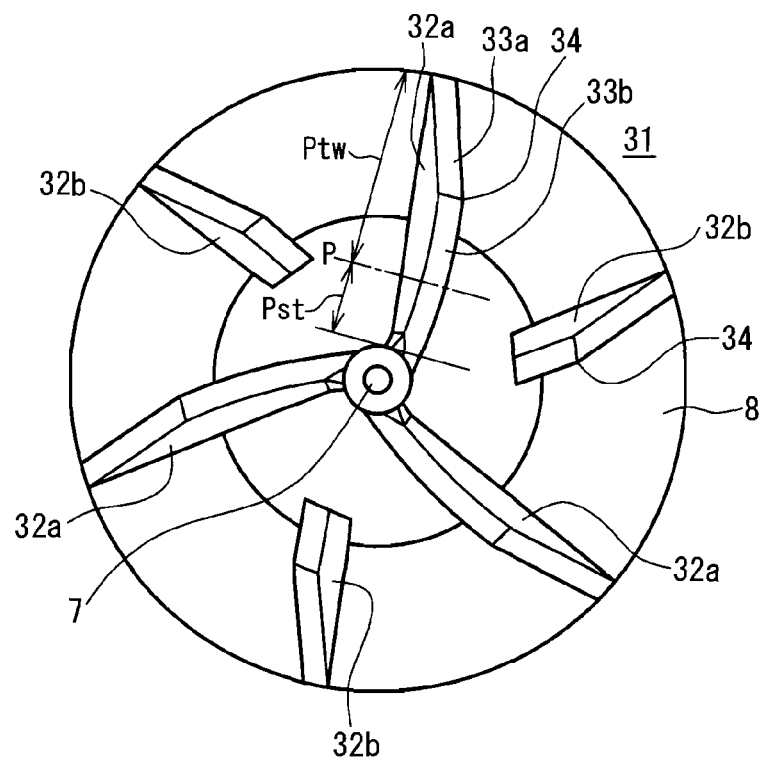
FIG. 2 is a top view of an impeller of the turbo blood pump of FIG. 1.
Figure 3:
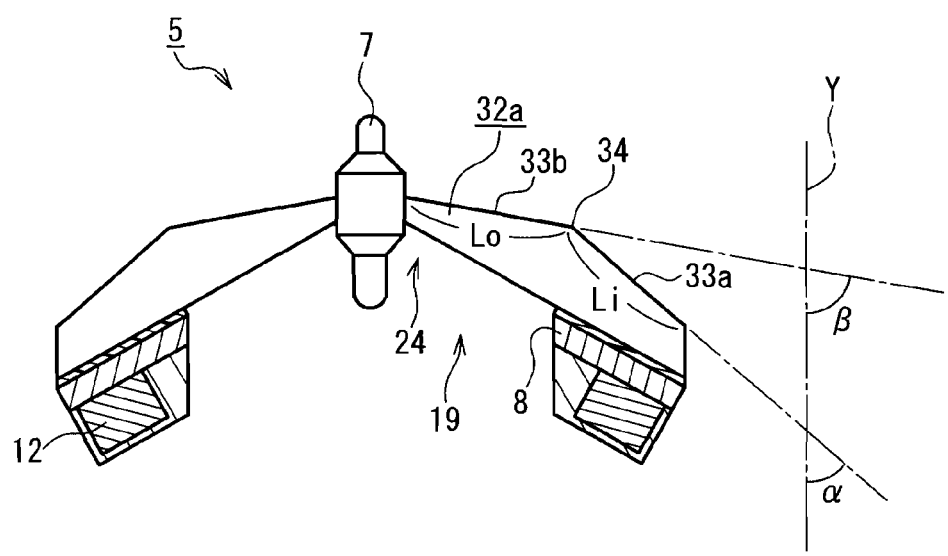
FIG. 3 is a cross-sectional view of the impeller of the turbo blood pump of FIG. 1.

In the blood pump of the present embodiment, a housing 30 and an impeller 31 have forms improved from the conventional example. FIG. 2 is a top view of the impeller 31, and FIG. 3 is a cross-sectional view thereof. As shown in FIG. 2, six vanes include main vanes 32a and sub vanes 32b, which are placed alternately. The main vanes 32a and the sub vanes 32b are referred to as the vanes 32 collectively. It should be noted that all the vanes 32 may be formed as the main vanes 32a instead of being divided into the main vanes 32a and the sub vanes 32b. The cross-sectional shape of the vane 32 in FIGS. 1 and 3 is taken along only the main vane 32a in FIG. 2 for the sake of convenience. The vane 32 basically has a twisted three-dimensional curved surface shape in the same way as in the vane 6 shown in FIG. 7B.

Figure 6:
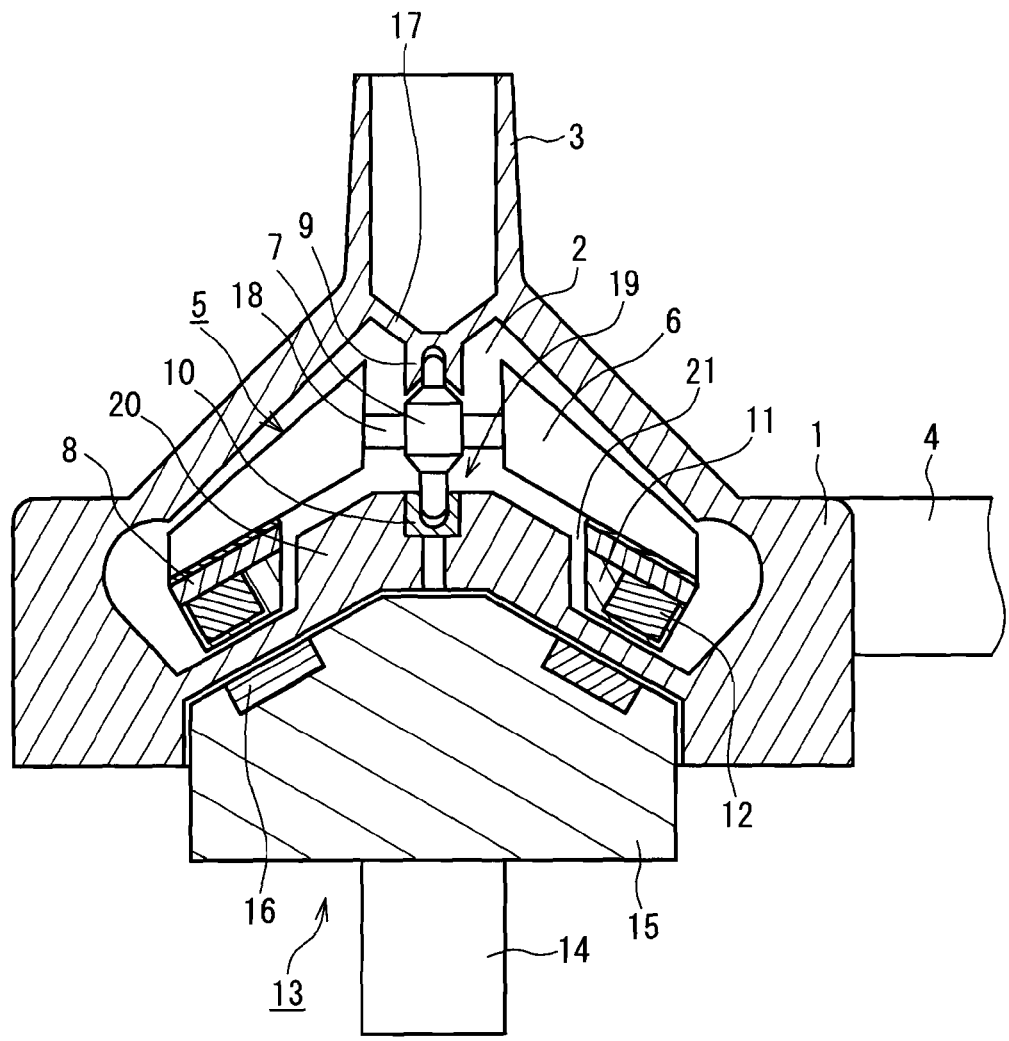
FIG. 6 is a cross-sectional view of a turbo blood pump in a conventional example.
Figure 7A:
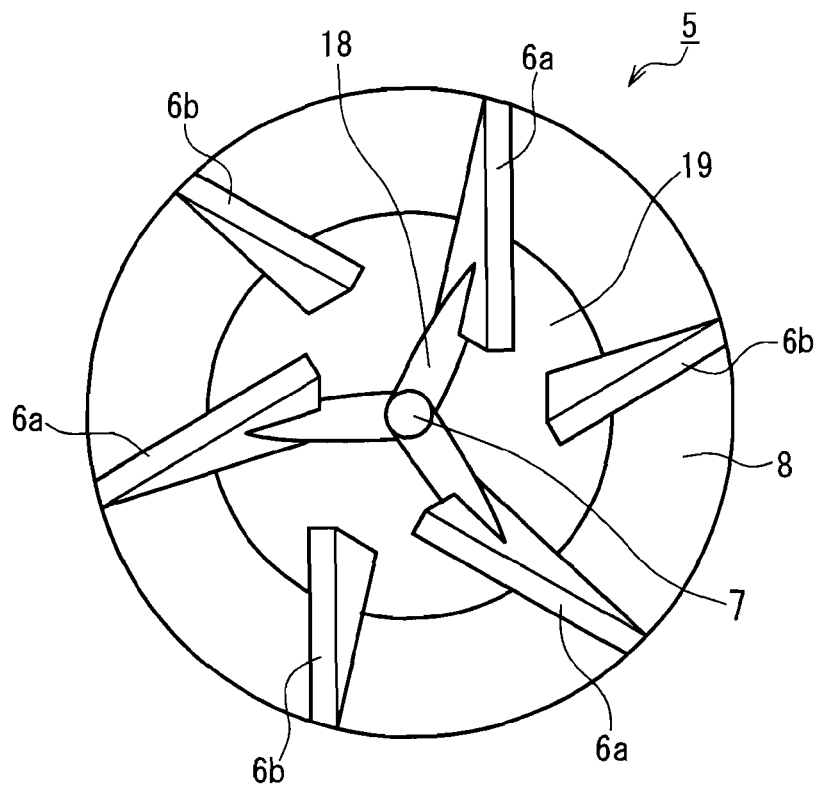
FIG. 7A is a top view of an impeller of the turbo blood pump of FIG. 6.
Figure 7B:
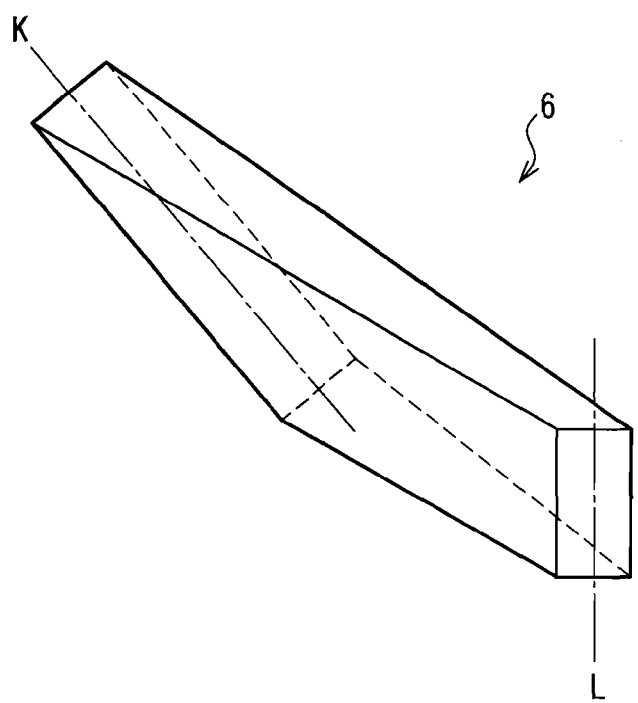
FIG. 7B is a perspective view showing the shape of one vane in the impeller of FIG. 7A.
Figure 8:
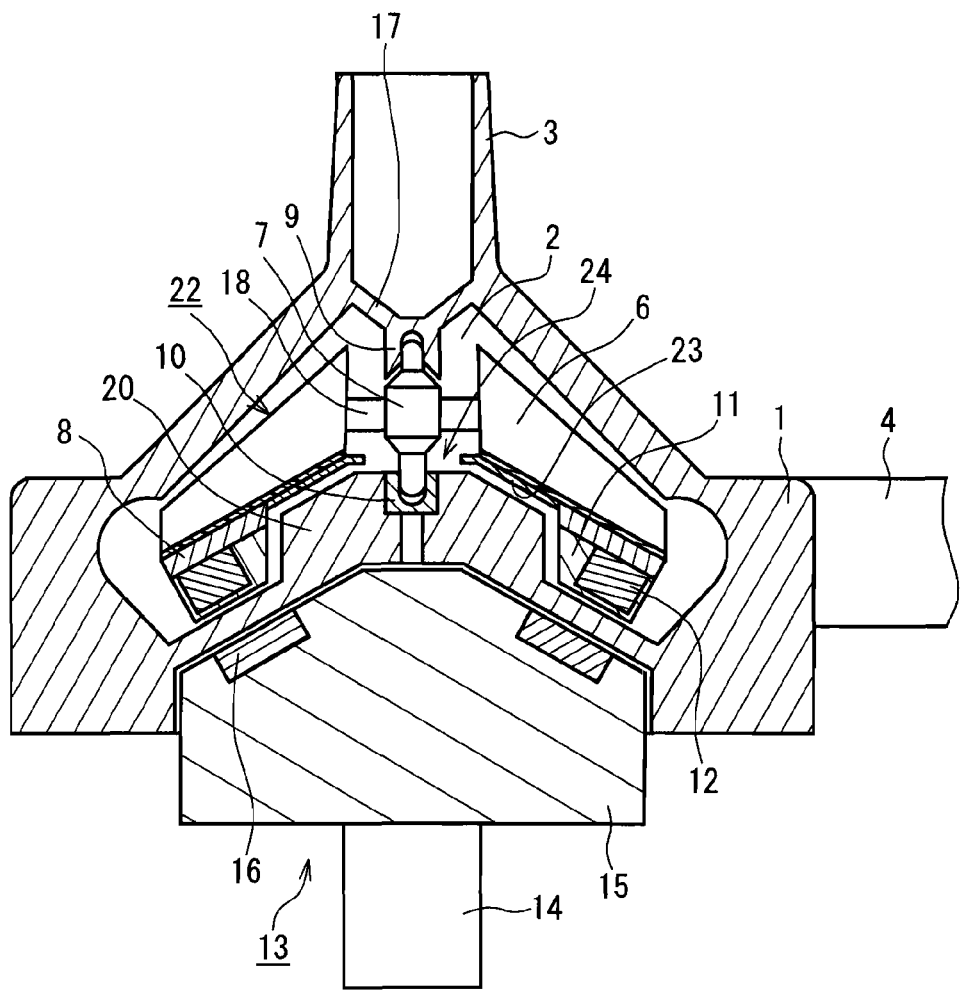
FIG. 8 is a cross-sectional view of a turbo blood pump in another conventional example.
Figure 9:
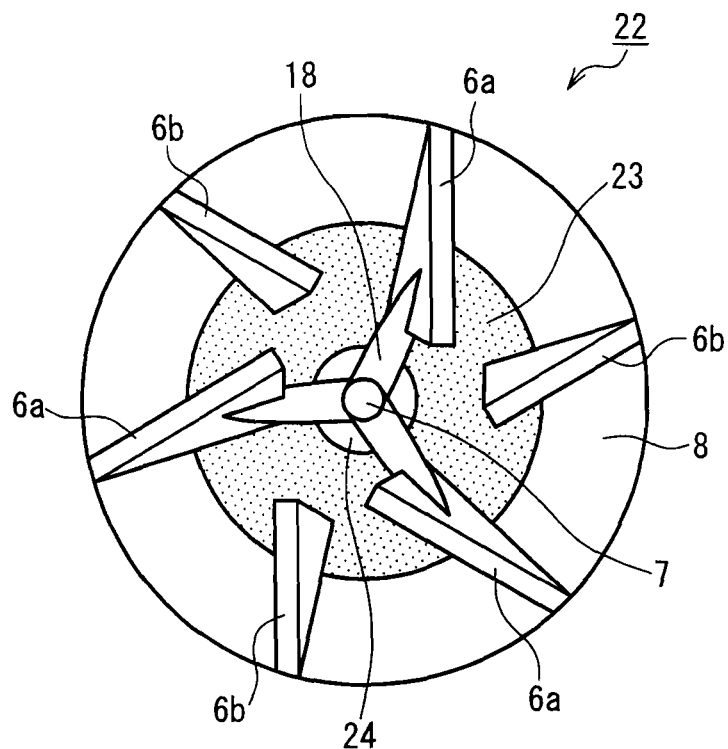
FIG. 9 is a top view of an impeller of the turbo blood pump of FIG. 8.
Figure 10:
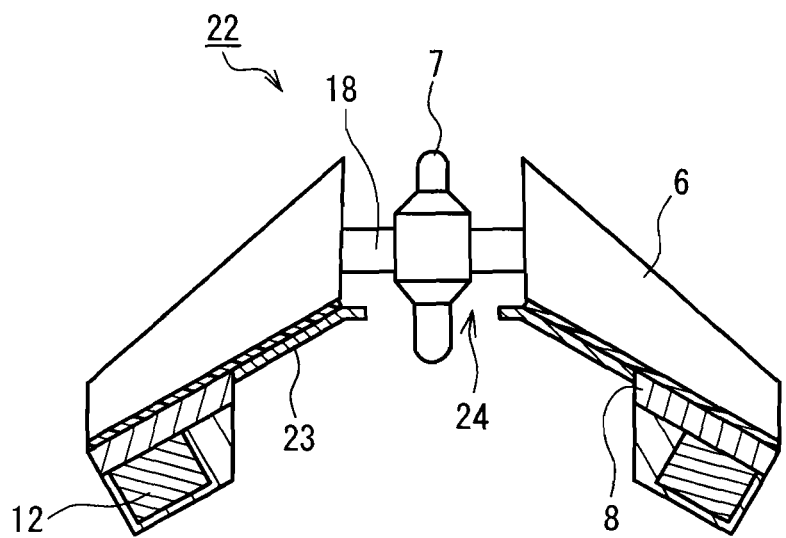
FIG. 10 is a cross-sectional view of the impeller of the turbo blood pump of FIG. 8.

In the present embodiment, the ends of the main vanes 32a on a center side extend so as to be coupled to the rotating shaft 7 directly without using the arms 18 as in the conventional example shown in FIGS. 6, 7A, etc. In the same way as in the conventional example, the ends of the sub vanes 32b on the center side are free ends not being coupled to the rotating shaft, and only the ends thereof on a circumferential edge side are coupled to an annular coupling portion 8.

As is clearly shown in the figure, the upper edge of each of the vanes 32 (both the main vanes 32a and the sub vanes 32b) has a bend point 34 whose position in the shaft direction of the rotating shaft 7 changes. An outer circumferential edge side with respect to the bend point 34 is referred to as a peripheral upper vane edge 33a, and a center side with respect to the bend point 34 is referred to as a central upper vane edge 33b.

As shown in FIG. 3, an angle formed by the peripheral upper vane edge 33a relative to the downward direction Y parallel to the rotating shaft 7 is defined as a peripheral upper vane edge angle $\alpha$, and an angle formed by the central upper vane edge 33b relative to the downward direction of the direction Y is defined as a central upper vane edge angle $\beta$. The peripheral upper vane edge angle $\alpha$ and the central upper vane edge angle $\beta$ are both acute angles and have a relationship of $\alpha<\beta$. In other words, the central upper vane edge 33b forms an inclination closer to a horizontal direction, compared with the peripheral upper vane edge 33a.

In accordance with the shape of the upper edge of the vane 32 as described above, particularly, in the region opposed to the central upper vane edge 33b, the inner wall surface of a pump chamber 35 of the housing 30 has a shape following the central upper vane edge 33b. As a result of the central upper vane edge 33b becoming closer to a horizontal shape, the inner wall surface of the housing 30 having a shape following the central upper vane edge 33b and the upper bearing 9 have a closer positional relationship. Therefore, an inlet port 3 is also placed close to the upper bearing 9, and hence, at least a part of bearing pillars 17 and the upper bearing 9 is placed in the inlet port 3.

As described above, each vane 32 has the bent point 34, the central upper vane edge angle $\beta$ is larger than the peripheral upper vane edge angle $\alpha$, and the inner wall surface of the pump chamber 35 of the housing 30 has a shape following the central upper vane edge 33b, whereby a gap between an upper portion of the impeller 31 and a inner wall surface in an upper portion of the housing 30 becomes small. As a result, the flow state in the vicinity of the upper bearing 9 is improved, and the effect of cleaning by a blood stream is enhanced. This is because a so-called secondary flow of blood that has received an ejection force by the impeller 31 reaches the vicinity of the upper bearing 9 easily. The secondary flow of blood means a flow of blood that comes out of the outlet side of the vanes 32, passes through the gap between the upper surface of the impeller 31 and the inner wall surface of the pump chamber 35 of the housing 30, and returns to the inlet side of the vanes 32.

According to the above-mentioned configuration, although the area of a vane surface in an upper portion of the vane 32 is reduced, the upper portion of the impeller 31 hardly influences the ejection. Therefore, the influence on an ejection force is not significant.

In order to obtain the above-mentioned effect, it is desired that the vane upper edge angle $\alpha$ is set in a range of 30° to 60°, and the vane upper edge angle $\beta$ is set in a range of 70° to 90°.

It is desired that a ratio Lo/Li is set in a range of 0.75 to 3.20, where Lo represents a length of a region of the central upper vane edge 33b and Li represents a length of a region of the peripheral upper vane edge 33a in the radial direction of the impeller 31.

Further, in order to improve the flow state in the vicinity of the upper bearing 9, it is desired that the end on the center side extends to the rotating shaft 7 as in the main vanes 32a. Thus, the flow state of the impeller 31 in the center portion becomes satisfactory. In this connection, it should be noted that the vane 32 has a twisted three-dimensional curved surface shape in the same way as in the vane 6 shown in FIG. 7B. Therefore, when the main vane 32a extends to be directly coupled to the rotating shaft 7, if the center side of the main vane 32a extends with the conventional twist of the vane 32 retained, the end of the main vane 32a on the center side comes off from the rotating shaft 7, which makes the coupling therebetween difficult.

In the present embodiment, as shown in FIG. 2, the main vane 32a is divided into a twisted portion on an outlet side (outer edge side of the impeller 31) and a linear portion on an inlet side (center side of the impeller 31) with respect to a predetermined position P in the longitudinal direction. More specifically, the above-mentioned twist is formed from the outer edge end of the main vane 32a to the position P in a direction to the inner edge end, and a linear shape is formed without a twist on the center side from the position P. This enables the end of the main vane 32a on the center side to be coupled to the rotating shaft 7 easily.

By designing only a portion of the main vane 32a which influences the ejection ability of a pump and hemolysis with the same configuration as that of the conventional example and allowing a portion that extends to the rotating shaft 7 to extend linearly with a twist eliminated, the flow state in the center portion of the impeller 31 can be improved while the performance of a pump, such as ensuring a blood transmission amount (ejection ability) and the reduction in hemolysis, are kept. In order to obtain the above-mentioned effects, it is important to determine the position P. When the length of (the linear portion corresponding to) the twisted portion of the main vane is defined as Ptw and the length of the linear portion of the main vane is defined as Pst, as shown in FIG. 2, it is desired to adjust the position P so as to satisfy a relationship: $0.58<Ptw/(Ptw+Pst)<0.80$.

In order to obtain the effect of suppressing the formation of a blood clot by enhancing the effect of cleaning by a blood stream in the vicinity of the upper bearing 9 in the turbo blood pump of the present embodiment as described above, it is most effective to provide the bend point 34 on the upper edge of the vane 32 with the central upper vane edge angle β set to be larger than the peripheral upper vane edge angle α, and reduce the gap between the upper portion of the impeller 31 and the inner wall surface of the housing 30.

In addition, the flow state in the vicinity of the upper bearing 9 becomes more satisfactory, and the effect of suppressing the formation of a blood clot is further enhanced by designing the configuration in which the end of the main vane 32a on the center side extends to the rotating shaft 7.

Embodiment 2

Figure 4:
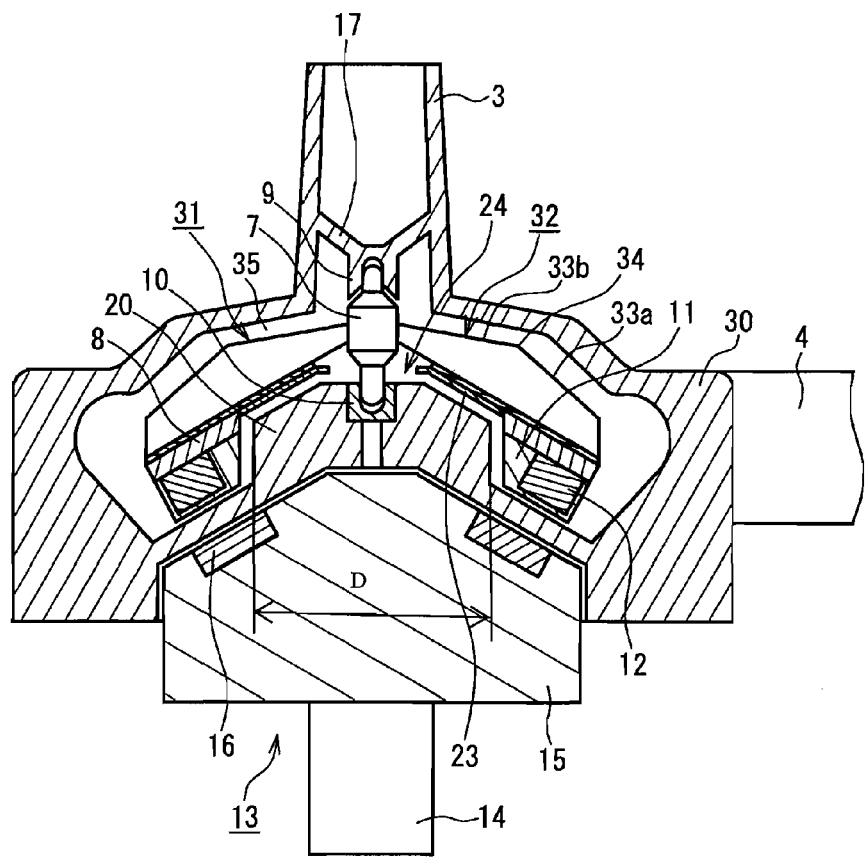
FIG. 4 is a cross-sectional view of a turbo blood pump in Embodiment 2 of the present invention.

FIG. 4. is a cross-sectional view showing a turbo blood pump in Embodiment 2 of the present invention. The basic configuration of the turbo blood pump is the same as that of Embodiment 1 shown in FIG. 1. Therefore, the same elements as those shown in FIG. 1 are denoted with the same reference numerals as those therein, and repeated description thereof are omitted.

Figure 5:
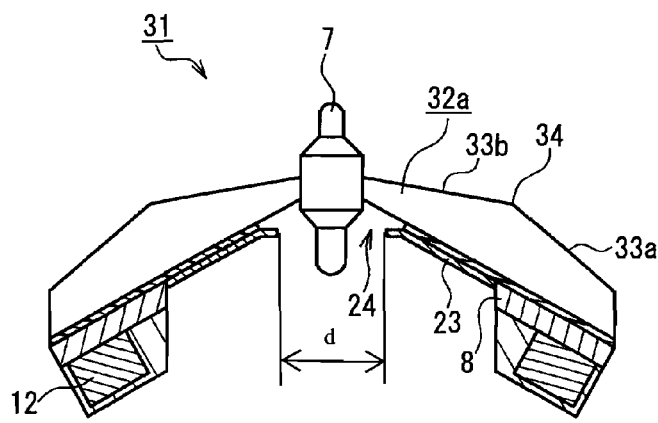
FIG. 5 is a cross-sectional view of an impeller of a turbo blood pump of FIG. 4.

The blood pump of the present embodiment has a configuration in which a blockade member 23 as shown in the conventional example of FIGS. 8 to 11 is added to the configuration of Embodiment 1. FIG. 5 is a cross-sectional view of an impeller 31 in the turbo blood pump of FIG. 4.

As shown in FIGS. 4 and 5, the impeller 31 includes vanes 32 having the same configuration as that of Embodiment 1 and has the blockade member 23 placed below the vanes 32 in a region spreading between a rotating shaft 7 and an annular coupling portion 8. The blockade member 23 blocks a flow path passing between a space in the region, which spreads between the rotating shaft 7 and an annular coupling portion 8, and the vanes 32, while leaving a part of an opening 24 around the rotating shaft 7. By providing the blockade member 23, the formation of a blood clot around the rotating shaft 7, for example, in the vicinity of a lower bearing 10 on the upper surface of a base 20 can be suppressed.

More specifically, by providing the blockade member 23, the blood in the gap between the impeller 31 and the bottom surface of the housing 30 flows toward the center of the impeller 31 along the lower surface of the blockade member 23, and thereafter, rises through the opening 24 of the blockade member 23. At this time, a blood stream with a sufficient flow rate is formed adjacent to the lower bearing 10 along the rotating shaft 7, which prevents the stagnation of blood. Thus, the vicinity of the lower bearing 10 is ready to be washed away at all times, so that the formation of a blood clot is suppressed.

On the other hand, in the same way as in Embodiment 1, by providing a bend point 34 on the upper edge of the vane 32 with a central upper vane edge angle β set to be larger than a peripheral upper vane edge angle α, and reducing the gap between the upper portion of the impeller 31 and the inner wall surface of the housing 30, the effect of cleaning by a blood stream in the vicinity of the upper bearing 9 is enhanced, and the effect of suppressing the formation of a blood clot is improved. It is desired to add a configuration in which the end of the main vane 32a on the center side extends to the rotating shaft 7, which further enhances the effect of cleaning in the vicinity of the upper bearing 9 while keeping pump performance.

As described above, the effect of cleaning by a blood stream in the vicinity of the upper bearing 9 and the lower bearing 10 is enhanced, and the effect of suppressing the generation of a blood clot becomes sufficient practically in the entire turbo blood pump, by improving the shape of the upper edge of the vane 32 and providing the blockade member 23.

Next, the results of an experiment for setting the conditions of the opening 24 of the blockade member 23 will be described. As a test solution for evaluating the formation of a blood clot, liquid in which oil is mixed in a weight ratio of 4 with respect to 6 of oil paints is used. The test solution is circulated by driving a pump while changing a diameter d of the opening 24 of the blockade member 23 in the configuration of the turbo blood pump shown in FIG. 4, whereby the size of an oil film formed on the upper surface of the base 20 is checked.

A diameter D of a cylindrical surface of the base 20, a diameter of the rotating shaft 7, and a diameter of an inner circumferential surface of the annular coupling portion 8 are set to be 20 mm, 2 mm, and 22 mm, respectively. Thus, the diameter d of the opening 24 is changed in a range of 2 mm to 22 mm. A pump flow rate is set to be 2.0 L/min, a rotation speed is set to be 4,000 $min^{-1}$, and a circulation time is set to be 2 minutes.

The ratio of the remaining oil film starts decreasing from the vicinity of 13 mm along with the reduction in the diameter d of the opening 24 from 22 mm (without the blockade member 23). When the diameter d reaches 6 mm, the effect of decreasing the remaining oil film obtained by reducing the diameter d becomes gentle. The effect of decreasing the remaining oil film is largest with the diameter d in a range of 2.4 mm to 4.5 mm. When the diameter becomes smaller than 2.4 mm, the ratio of the remaining oil film increases, in contrast. This is because the flow path of blood becomes too small.

As described above, the optimum diameter d of the opening 24 for suppressing the formation of a blood clot is in a range of 2.4 mm to 4.5 mm. On the other hand, even when the diameter d of the opening 24 is set to be larger than the above-mentioned optimum range, that is, more than 4.5 mm (i.e., 6 mm), considering the other conditions, the effect of suppressing the formation of a blood clot is obtained sufficiently for practical purposes. Although the suitable range of the diameter d of the opening 24 varies slightly depending upon the size of the turbo blood pump, desired effects can be obtained as long as turbo blood pumps in a generally used range are standardized as described below.

Specifically, the diameter d of the opening 24 may be set in a range of $0.12D \leq d \leq 0.3D$, preferably $0.12D \leq d \leq 0.225D$ with respect to the diameter D of the cylindrical surface of the base 20.

INDUSTRIAL APPLICABILITY

In the turbo blood pump of the present invention, the effect of cleaning by a blood stream in the vicinity of an upper bearing supporting an impeller is enhanced to suppress the formation of a blood clot. Therefore, the turbo blood pump is suitable as a blood pump for conducting extracorporeal blood circulation in an artificial heart and lung apparatus and the like.

DESCRIPTION OF REFERENCE NUMERALS 1, 30 housing
2, 35 pump chamber
3 inlet port
4 outlet port 5, 22, 31 impeller
6, 32 vane
6a, 32a main vane
6b, 32b sub vane
7 rotating shaft
8 annular coupling portion
9 upper bearing
10 lower bearing
11 magnetic case
12 driven magnet
13 rotor
14 drive shaft
15 magnetic coupling portion
16 drive magnet
17 bearing pillar
18 arm
19 space
20 base
21 gap portion
23 blockade member
24 opening
33a peripheral upper vane edge
33b central upper vane edge
34 bend point

The invention claimed is:

1. A turbo blood pump, comprising:
a housing having a pump chamber, an inlet port, and an outlet port;
an impeller supported rotatably in the pump chamber;
a rotatable rotor provided in an outside lower portion of the housing; and
a drive force transmitting element for rotating the impeller,
the impeller including: a rotating shaft supported rotatably by an upper bearing and a lower bearing at upper and lower ends; a plurality of vanes connected to the rotating shaft on an inner circumferential edge side; an annular coupling portion coupling an outer circumferential edge side of each of the vanes; and a driven magnet portion placed in a lower portion of the annular coupling portion, in which the inlet port is positioned above the upper bearing and the outlet port is positioned at a lateral outside of a periphery of the pump chamber,
the drive force transmitting element being formed of magnetic coupling between the driven magnet portion and a drive magnet portion provided at the rotor,
wherein an upper edge of each of the vanes is bent so as to form a peripheral upper vane edge on an outer circumferential edge side with respect to a bend point and a central upper vane edge on a center side with respect to the bend point,
when a peripheral upper vane edge angle α is defined as an angle formed by the peripheral upper vane edge relative to a downward direction of the rotating shaft direction, and a central upper vane edge angle β is defined as an angle formed by the central upper vane edge relative to the downward direction of the rotating shaft direction, the peripheral upper vane edge angle α and the central upper vane edge angle β are both acute angles and have a relationship of α<β,
a ratio Lo/Li is set in a range of 0.75 to 3.20, where Lo represents a length of a region of the central upper vane edge and Li represents a length of a region of the peripheral upper vane edge in a radial direction of the impeller, and
an inner wall surface of the pump chamber of the housing in a region opposed to the upper edge of each of the vanes has a bent portion corresponding to the upper edge of each of the vanes, with the upper bearing that supports the rotating shaft being disposed between the inlet port and bent portion, thereby enhancing an effect of a secondary flow of blood toward the inlet port for suppressing formation of a blood clot in a vicinity of the upper bearing.

2. The turbo blood pump according to claim 1, wherein at least a part of the upper bearing is placed in the inlet port.

3. The turbo blood pump according to claim 1, wherein an inner circumferential edge side of each of the vanes extends to a position of the rotating shaft in such a manner that each of the vanes is coupled to the rotating shaft directly.

4. The turbo blood pump according to claim 3, wherein when a vane inlet line K is defined as a line segment connecting between an upper end of each of the vanes and a lower end thereof on an inlet side on which blood flowing from the inlet port comes into contact with the respective vane, and a vane outlet line L is defined as a line segment connecting between an upper end of each of the vanes and a lower end thereof on an outlet side on which blood leaves from the respective vane,
each of the vanes has a three-dimensional curved surface shape in which the vane inlet line K is twisted with respect to the rotating shaft, and the vane outlet line L is twisted with respect to the vane inlet line K, and
each of the vanes has a twisted shape in a range of a region on the outer circumferential edge side and forms a linear shape in a region on an inner circumferential edge side.

5. The turbo blood pump according to claim 4, wherein when a length of the region having the twisted shape on the outer circumferential edge side of the respective vane is defined as Ptw and a length of the region having the linear shape of the respective vane is defined as Pst,
the length Ptw and the length Pst are adjusted so as to satisfy a relationship: $0.58 < Ptw/(Ptw+Pst) < 0.80$.

6. The turbo blood pump according to claim 1, wherein the peripheral upper vane edge angle α is set in a range defined as $30° < α < 60°$, and the central upper vane edge angle β is set in a range defined as $70° < β < 90°$.

7. The turbo blood pump according to claim 1, wherein the impeller includes a blockade member placed below the vanes in a region spreading between the rotating shaft and the annular coupling portion, and
the blockade member blocks a space in the region spreading between the rotating shaft and the annular coupling portion while leaving an opening at least around the rotating shaft.

8. The turbo blood pump according to claim 7, wherein a base having a cylindrical outer circumferential surface which protrudes upward is formed at the center in a bottom portion of the housing so as to fill a space in a region of a lower portion of the impeller surrounded by a cylindrical inner circumferential surface formed by the annular coupling portion and the driven magnet portion, the base being provided with the lower bearing,
the opening of the blockade member has a circular shape concentric to the rotating shaft, and
when a diameter of the opening of the blockade member is d, and a diameter of the cylindrical outer circumferential surface of the base is D, the diameter d of the opening is set in a range of $0.12D ≤ d ≤ 0.3D$.

9. The turbo blood pump according to claim 1, wherein sub vanes are placed between the vanes, an outer circumferential edge side of each of the sub vanes being connected to the annular coupling portion and an inner circumferential edge side of each of the sub vanes being a free end.

10. The turbo blood pump according to claim 1, wherein a minimum distance formed between the central upper vane edge and the inner wall surface of the pump chamber of the housing is smaller than a minimum distance formed between the peripheral upper vane edge and the inner wall surface of the pump chamber of the housing.

* * * * *